US006631716B1

(12) United States Patent
Robinson et al.

(10) Patent No.: US 6,631,716 B1
(45) Date of Patent: Oct. 14, 2003

(54) DYNAMIC RESPIRATORY CONTROL

(75) Inventors: Terry E. Robinson, Palo Alto, CA (US); Wallace C. White, Menlo Park, CA (US); Nicholas R. Kalayjian, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/354,627

(22) Filed: Jul. 16, 1999

Related U.S. Application Data

(60) Provisional application No. 60/093,214, filed on Jul. 17, 1998.

(51) Int. Cl.[7] .......................... A61M 16/00; A62B 7/00; F16K 31/02
(52) U.S. Cl. .......................... 128/204.21; 128/205.24; 482/5; 482/13
(58) Field of Search ................. 128/204.21, 205.24; 482/5, 13, 111

(56) References Cited

U.S. PATENT DOCUMENTS 3,710,780 A * 1/1973 Milch .......................... 482/13
3,991,304 A 11/1976 Hillsman (List continued on next page.)

OTHER PUBLICATIONS

Chatham et al., "Through Range Computer Generated Inspiratory Muscle Training in Cystic Fibrosis," *J. Pediatric Pulmonology*, Suppl. No. 14, Aug. 1997, Abst. No. 340, p. 299.

Wong et al., "The Use of Active Breathing Control (ABC) to Minimize Breathing Motion during Radiation Therapy," *I. J. Radiation Oncology*, v.39, No. 2, Supplement, 1997, p. 164.

Rauterkus et al., (Sensormedics, Inc.) "The Mass Flow Sensor: A Closer Look,"*CardioPulmonary Review*, SensorMedics product literature, 1992.

Hans Rudolph, Inc., "Two–Way Non–Rebreathing Valves, T–Shape Configuration, Series 1410 Small, 2600 Medium, 2700 Large," Hans Rudolph Inc. product literature, 1995, 3 pages.

Chatham et al., "Repeated Inspiratory Manoeuvres Against Fixed Resistance with Biofeedback is More Effective than Standard Chest Physiotherapy in Aiding Sputum Expectoration in Cystic Fibrosis ," *J. Pediatric Pulmonology*, Suppl. No. 19, Oct. 1999, Abst. No. 439, p. 289, Wiley–Liss Inc. (John Wiley & Sons), New York.

(List continued on next page.)

*Primary Examiner*—Weilun Lo
*Assistant Examiner*—Joseph F. Weiss, Jr.
(74) *Attorney, Agent, or Firm*—Andrei D. Popovici

(57) ABSTRACT

A dynamic respiratory control device includes a fast-response valve capable of dynamically imposing multiple resistive loads on the flow of respiratory gas to and from a patient. The resistive loads are applied in response to measured flow rates, patient lung volumes, and/or mouthpiece pressures. The device can precisely constrain tidal breathing, provide precise volumetric control of the airway, and impose multiple specific inspiratory and/or expiratory loading functions to evaluate respiratory function. The device is useful for pulmonary function testing, CT and MRI imaging of the chest, combined CT imaging/interventional radiology, radiotherapy delivery to the thorax/abdomen, and/or as a resistive muscle trainer for weaning patients off ventilators and for respiratory muscle training.

37 Claims, 11 Drawing Sheets

U.S. PATENT DOCUMENTS

| | | | |
|---|---|---|---|
| 4,039,139 A | | 8/1977 | Bird |
| 4,305,418 A | * | 12/1981 | Jensen et al. ............... 137/219 |
| 4,317,374 A | * | 3/1982 | Casey ..................... 73/861.53 |
| 4,333,476 A | | 6/1982 | Downing, Jr. |
| 4,433,576 A | * | 2/1984 | Shih et al. ..................... 73/204 |
| 4,487,207 A | * | 12/1984 | Fitz .............................. 482/13 |
| 4,495,944 A | * | 1/1985 | Brisson et al. ................ 482/13 |
| 4,533,137 A | * | 8/1985 | Sonne ......................... 272/99 |
| 4,823,828 A | | 4/1989 | McGinnis |
| 5,044,362 A | * | 9/1991 | Younes .................. 128/204.21 |
| 5,107,830 A | * | 4/1992 | Younes .................. 128/204.18 |
| 5,203,872 A | * | 4/1993 | Naffziger ..................... 251/82 |
| 5,507,282 A | * | 4/1996 | Younes .................. 128/204.21 |
| 5,572,993 A | * | 11/1996 | Kurome et al. ......... 128/204.23 |
| 5,596,969 A | | 1/1997 | Lipinski ..................... 123/494 |
| 5,598,838 A | * | 2/1997 | Servidio et al. ....... 128/204.23 |
| 5,634,471 A | | 6/1997 | Fairfax et al. |
| 5,656,938 A | * | 8/1997 | Bennohr et al. ............. 324/706 |
| 5,788,665 A | * | 8/1998 | Sekins ......................... 604/19 |
| 5,823,186 A | * | 10/1998 | Rossen et al. ......... 128/204.21 |
| 5,839,433 A | * | 11/1998 | Higenbottam .......... 128/204.21 |
| 5,839,434 A | | 11/1998 | Enterline |
| 5,865,173 A | | 2/1999 | Froehlich |
| 5,881,723 A | * | 3/1999 | Wallace et al. ........ 128/204.21 |
| 5,913,239 A | * | 6/1999 | Morris, Jr. et al. ........ 73/118.2 |
| 5,915,381 A | * | 6/1999 | Nord ..................... 128/204.23 |
| 5,918,596 A | * | 7/1999 | Heinonen .............. 128/204.21 |
| 5,927,275 A | * | 7/1999 | Loser et al. ........... 128/205.24 |
| 6,109,027 A | * | 8/2000 | Schaefer ...................... 60/324 |
| 6,165,105 A | * | 12/2000 | Boutellier et al. ............. 482/13 |
| 6,467,479 B1 | * | 10/2002 | Albert et al. .......... 128/204.23 |

OTHER PUBLICATIONS

Chatham et al., "Repeated Inspiratory Manoeuvres Against Fixed Resistance with Biofeedback is More Effective than Standard Chest Physiotherapy in Aiding Sputum Expectoration in Cystic Fibrosis ," *J. Pediatric Pulmonology*, Suppl. No. 19, Oct. 1999 (2 pages), Wiley–Liss Inc. (John Wiley & Sons), New York.

* cited by examiner

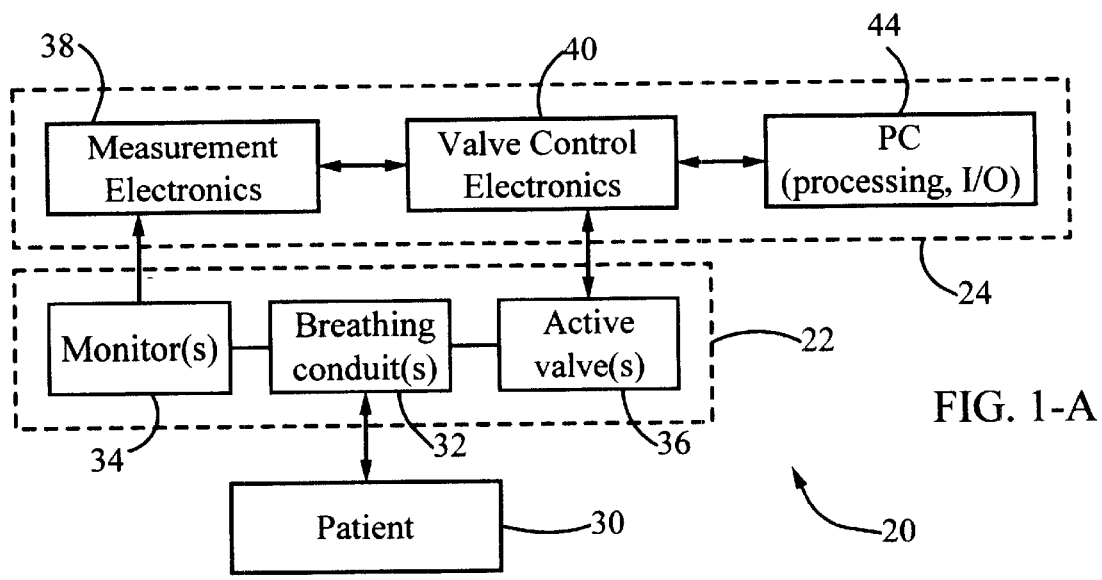
FIG. 1-A
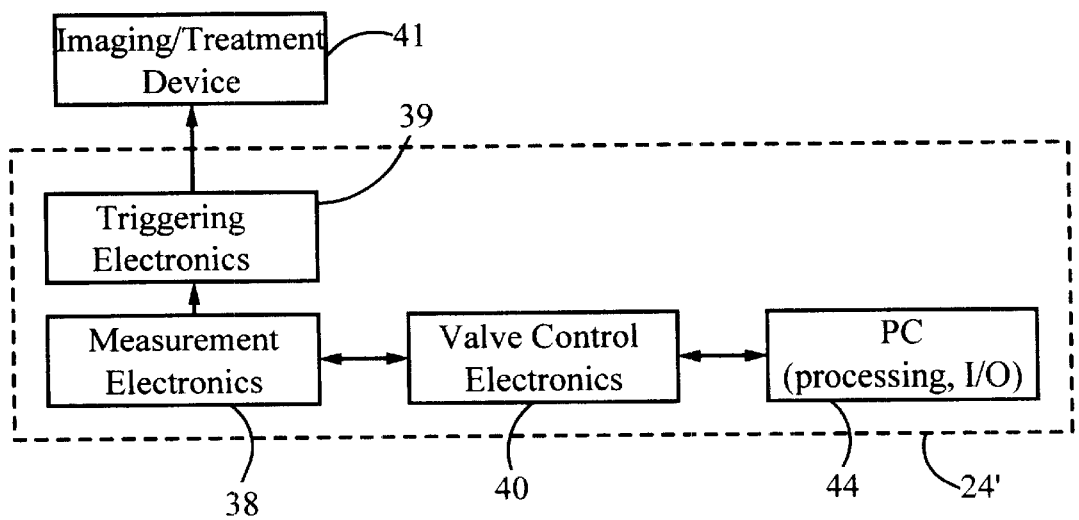
FIG. 1-B

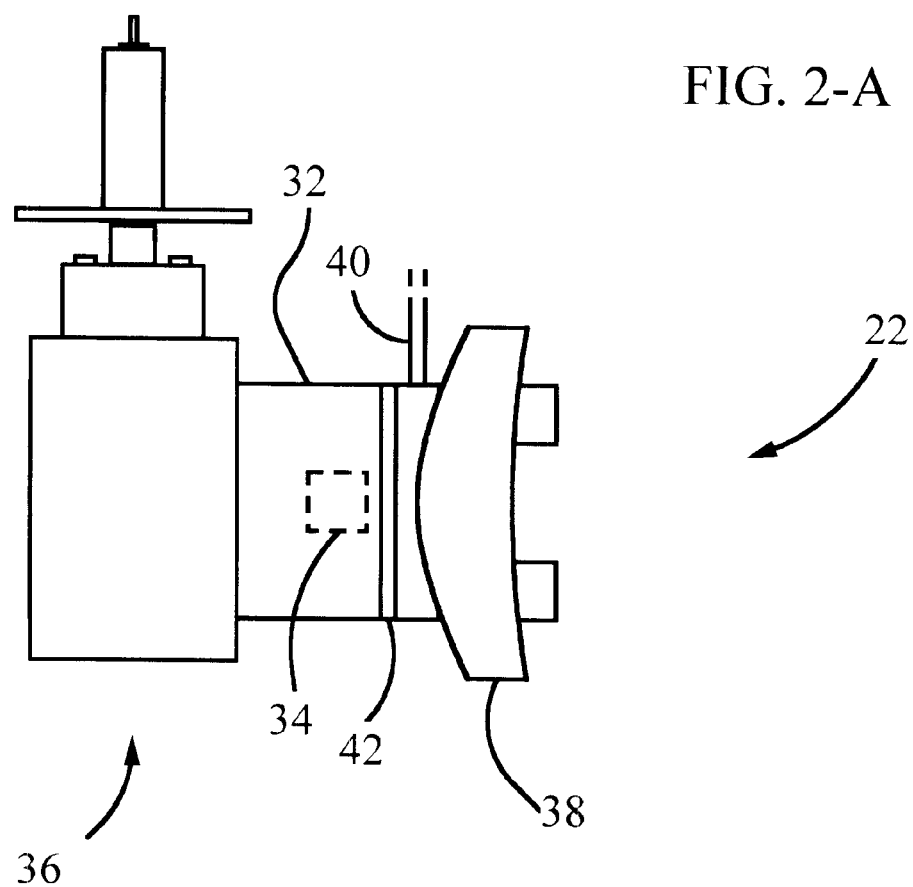
FIG. 2-A
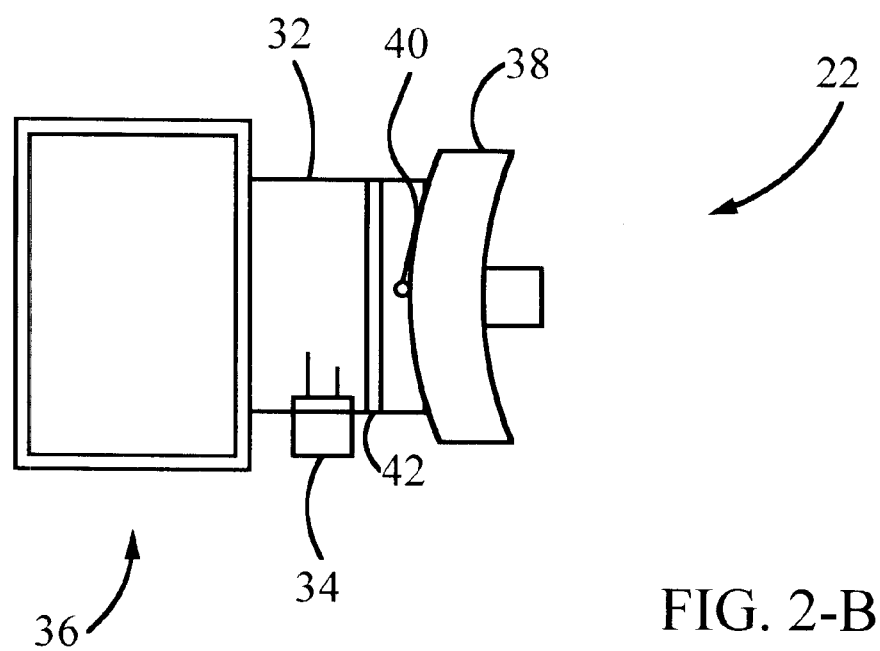
FIG. 2-B

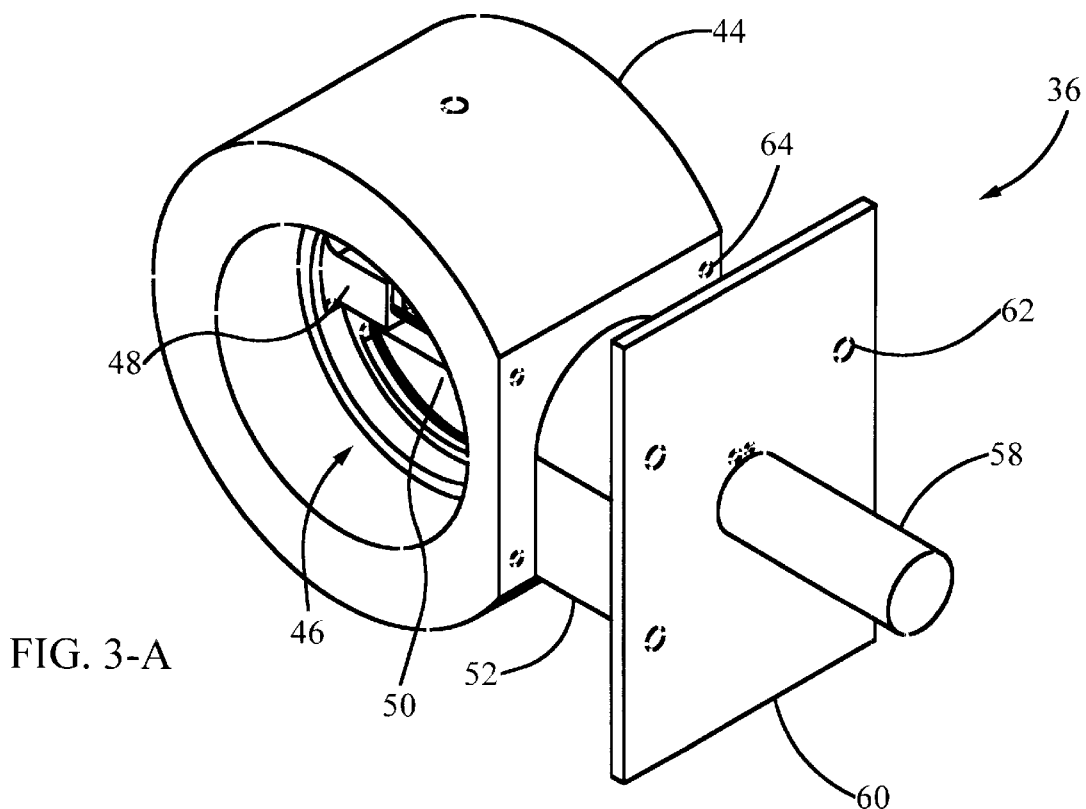
FIG. 3-A
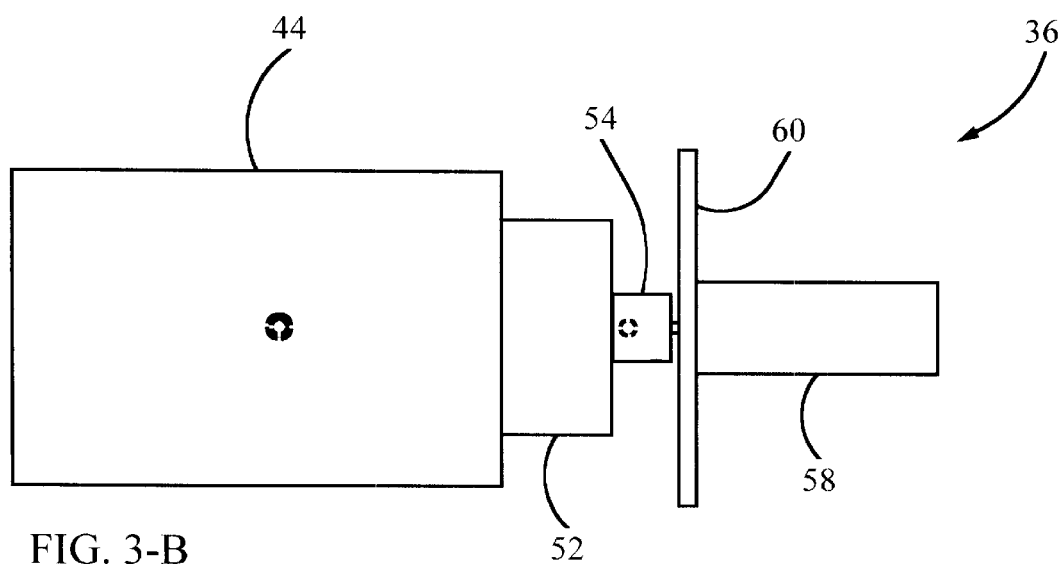
FIG. 3-B

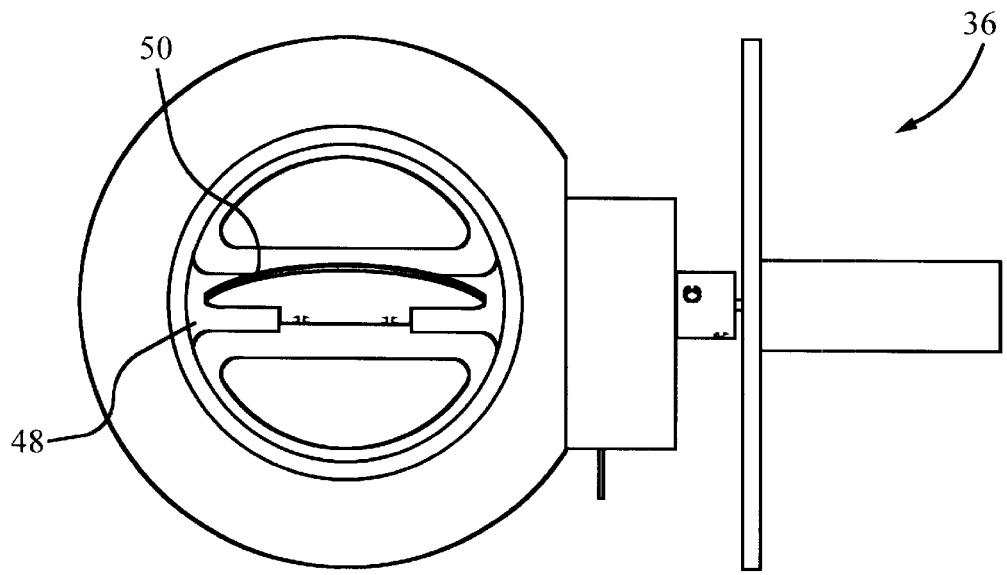
FIG. 4-A
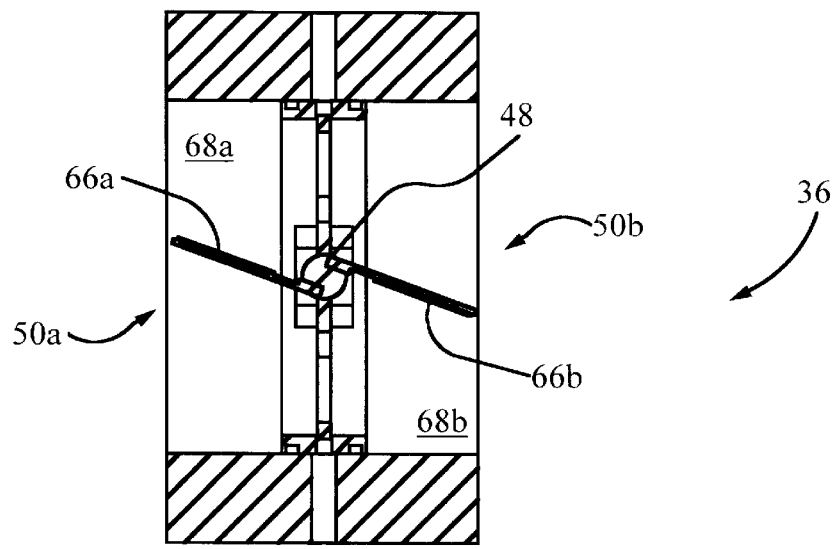
FIG. 4-B

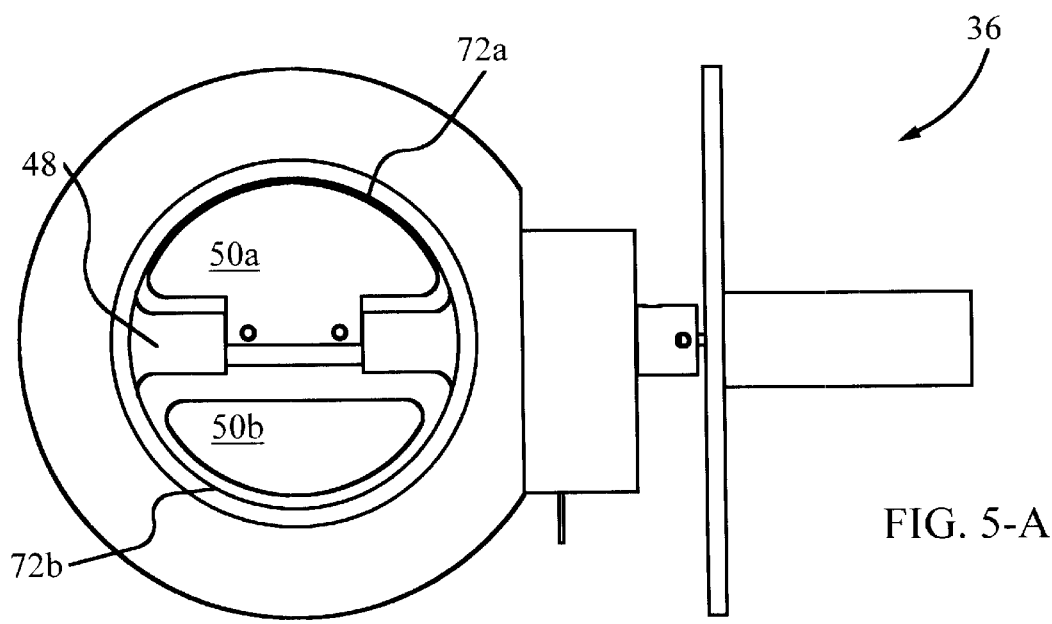
FIG. 5-A
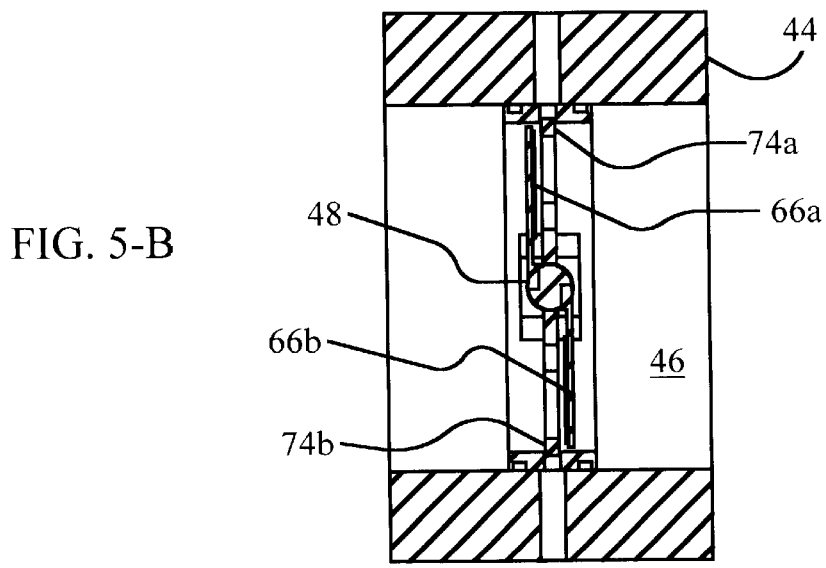
FIG. 5-B

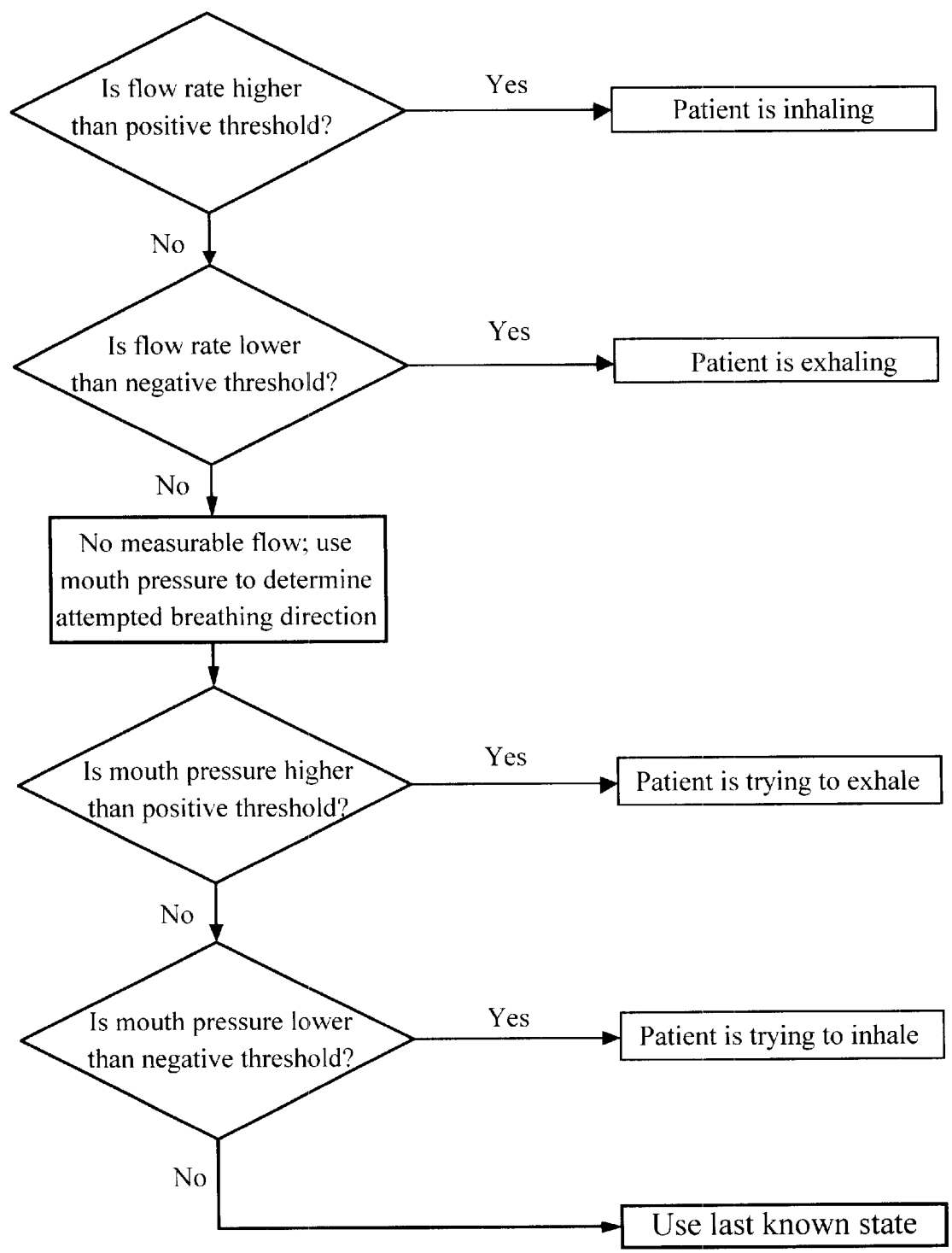
FIG. 6-A

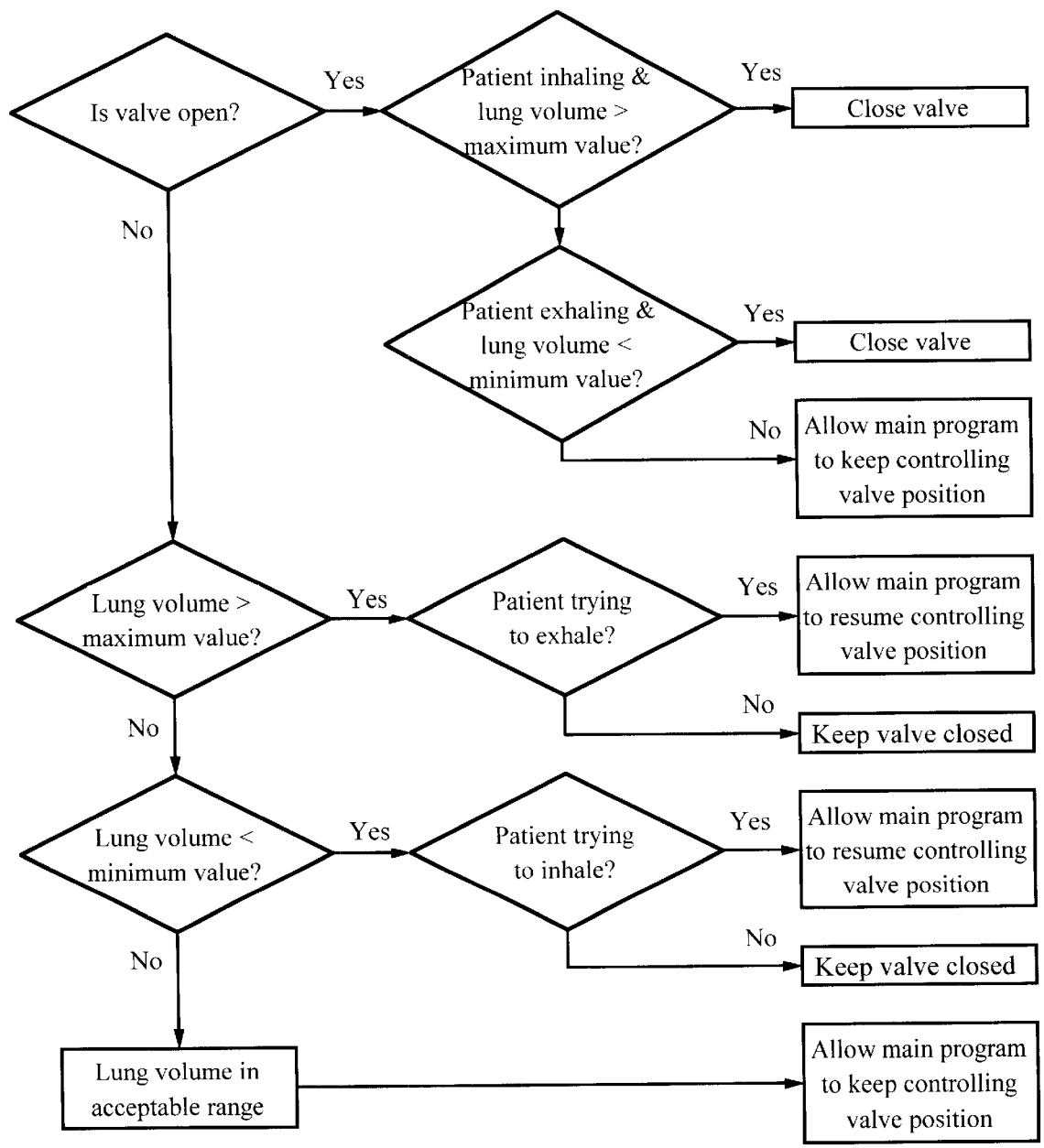
FIG. 6-B

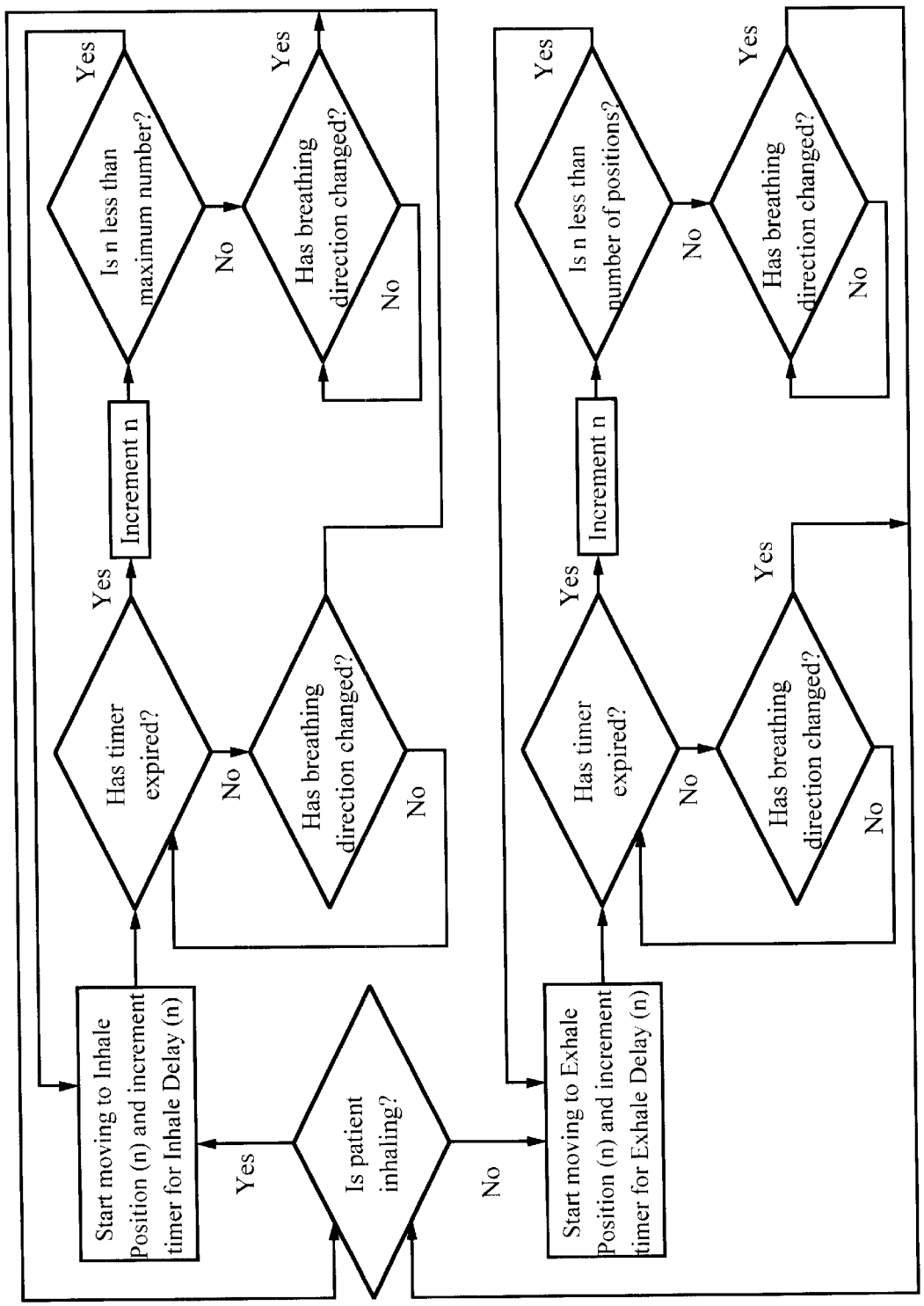
FIG. 6-C

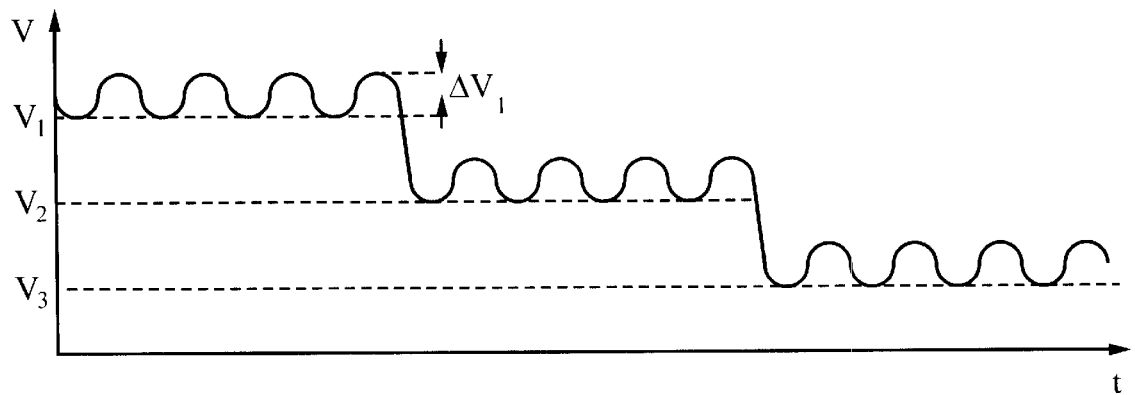
FIG. 7-A
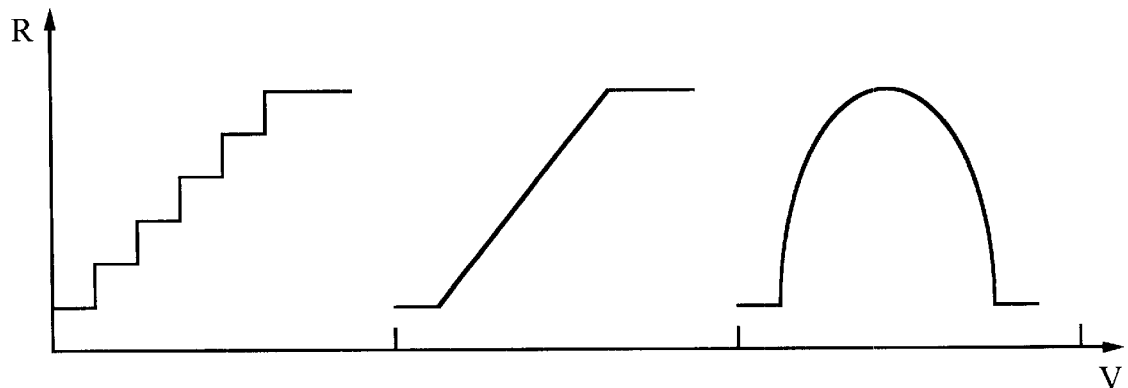
FIG. 7-B
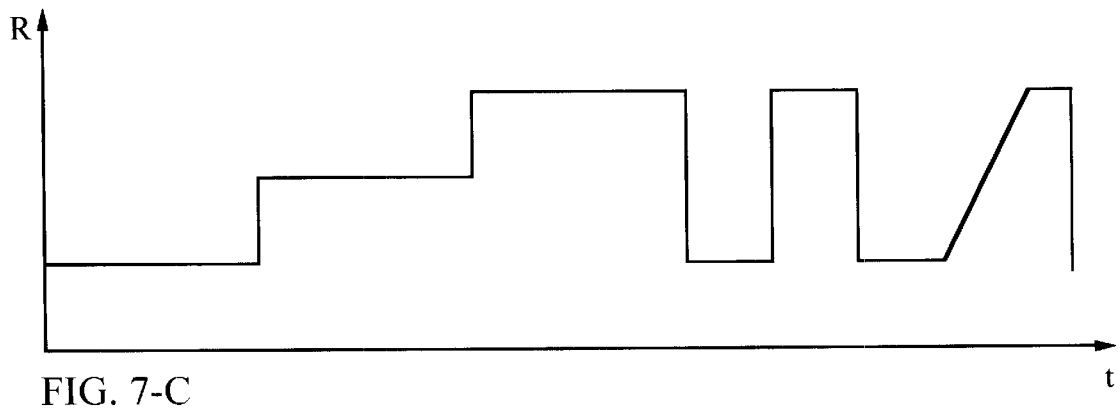
FIG. 7-C

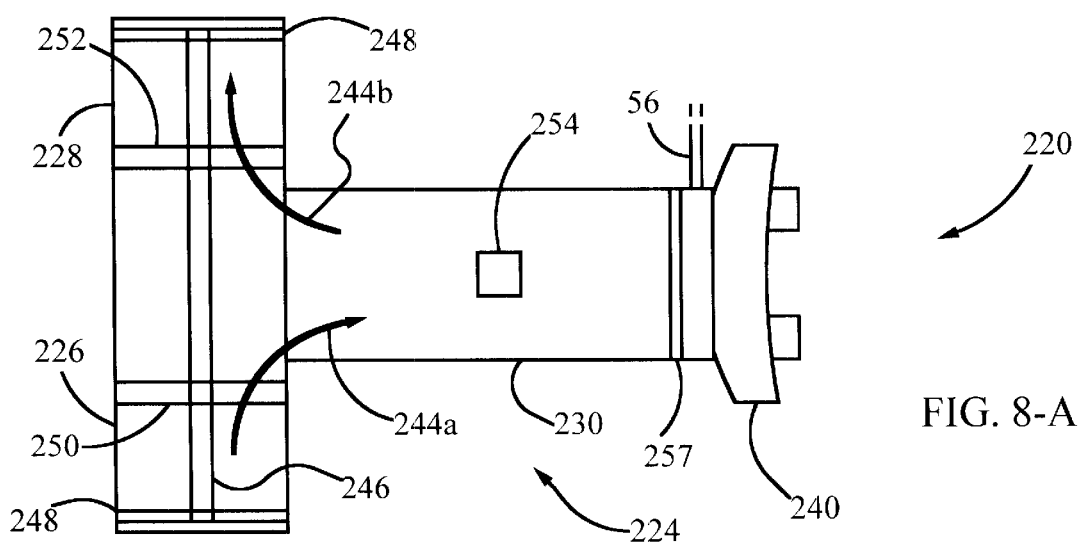
FIG. 8-A
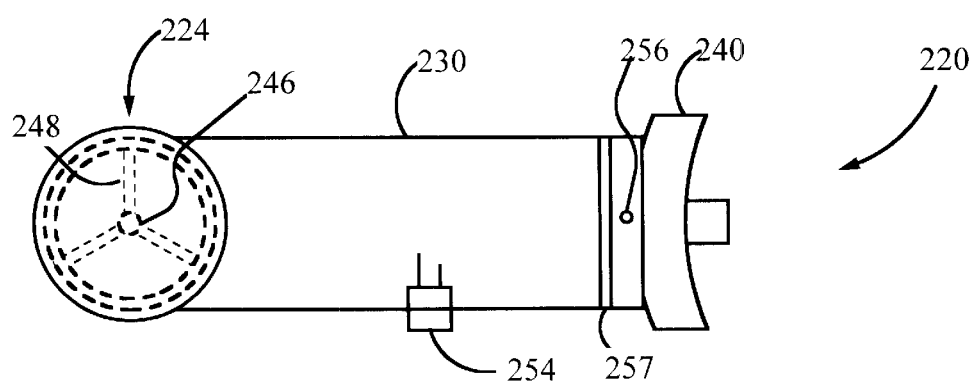
FIG. 8-B
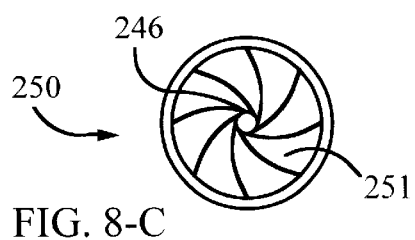
FIG. 8-C
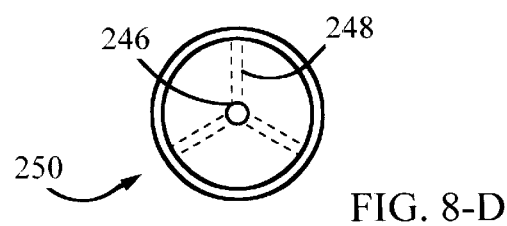
FIG. 8-D

_US 6,631,716 B1_

DYNAMIC RESPIRATORY CONTROL

RELATED APPLICATION DATA

This application is based on U.S. Provisional Patent Application No. 60/093,214, filed Jul. 17, 1998, which is herein incorporated by reference.

BACKGROUND

This invention relates to systems and methods for respiratory function analysis and control, and in particular to systems and methods for dynamically analyzing and controlling the respiration of a patient.

Controlling a patient's respiration is useful for many applications, including pulmonary function testing and evaluation, CT and MRI imaging of the chest, respiratory muscle training, and weaning patients off ventilators. Most currently available systems for controlling and evaluating respiratory function are relatively inflexible, and do not have the capability to precisely and dynamically control respiratory function. Moreover, some available methods of controlling respiratory function can be uncomfortable for the patient, particularly methods requiring the patient to hold his or her breath for extended periods of time.

SUMMARY

The present invention provides systems and methods for dynamically and accurately controlling a patient's respiratory function. The methods allow substantial flexibility in the evaluation process. The methods further allow limiting patient discomfort during respiratory function control procedures.

A dynamic respiratory control device includes a fast-response valve capable of dynamically imposing multiple resistive loads on the flow of respiratory gas to and from a patient. The resistive loads are applied according to measured flow rates, patient lung volumes, and/or mouthpiece pressures. The device can precisely constrain tidal breathing, provide precise volumetric control of the airway, and impose multiple specific inspiratory and/or expiratory loading functions to evaluate respiratory function. The device is useful for pulmonary is function testing, CT and MRI imaging of the chest, combined CT imaging/interventional radiology, radiotherapy delivery to the thorax/abdomen, and/or as a resistive muscle trainer for weaning patients off ventilators and for respiratory muscle training.

The present invention provides a dynamic respiratory control apparatus comprising: a respiratory function valve for dynamically controlling a respiratory gas flow for a patient; a flow rate monitoring device positioned in a flow path of the respiratory gas, in fluidic communication with the valve, for measuring a flow rate of the respiratory gas; and a control unit electrically connected to the monitoring device and the valve, for receiving flow rate data from the monitoring device and for dynamically controlling the valve to apply an intermediate resistive load to the flow according to the flow rate data. Further provided is a dynamic respiratory control method comprising: generating flow rate data characterizing a flow of a respiratory gas between a respiratory function valve and a patient; and dynamically controlling the valve to apply an intermediate resistive load to the flow according to the flow rate data. The real-time feedback and flexibility in applying multiple inspiratory and/or expiratory resistive loads allow improved respiratory function evaluation and control, as well as improved respiratory muscle training.

The present invention further provides a control unit electrically connected to the monitoring device and the valve, for receiving flow rate data from the monitoring device, determining a lung volume of the patient from the flow rate data, and dynamically controlling the valve to maintain the lung volume between a first predetermined value and a second predetermined value. Further provided is a dynamic respiratory control method comprising: generating flow rate data characterizing a flow of a respiratory gas between a respiratory function valve and a patient; determining a lung volume of the patient from the flow rate data; and dynamically controlling the valve to maintain the lung volume between a first predetermined value and a second predetermined value. Actively maintaining the patient's lung volume between two predetermined values allows limiting the range of motion of the patient's organs during imaging or therapy procedures, without requiring the patient to hold his or her breath.

DESCRIPTION OF THE FIGURES

FIG. 1-A is a schematic diagram of a preferred dynamic respiratory control system of the present invention.

FIG. 1-B shows a schematic diagram of control electronics and an imaging/treatment device according to an embodiment of the present invention.

FIGS. 2-A and 2-B show schematic top and side views, respectively, of a respiratory control device comprising an active valve according to the preferred embodiment of the present invention.

FIGS. 3-A and 3-B illustrate isometric and top views, respectively, of the active valve of FIG. 2-A.

FIGS. 4-A and 4-B show front and top sectional view, respectively, of the valve of FIG. 3-A in an open position.

FIGS. 5-A and 5-B show front and top sectional view, respectively, of the valve of FIG. 3-A in a closed position.

FIGS. 6-A–C are flowcharts illustrating a method of controlling a patient's lung volume between two predetermined values, according to the present invention.

FIG. 7-A shows the variation of patient lung volume with time over multiple breaths for a method in which the patient's lung volume is constrained between predetermined values, according to the present invention.

FIG. 7-B shows three potential variations of resistive loads with lung volume over part of one breath, according to the present invention.

FIG. 7-C shows potential patterns for time variations in resistive loads over multiple breaths, suitable for respiratory muscle training according to the present invention.

FIGS. 8-A and 8-B show top and side schematic views, respectively, of a respiratory control device having two active iris valves, according to an alternative embodiment of the present invention.

FIGS. 8-C and 8-D illustrate an iris valve of the device of FIG. 8-A in closed and open positions, respectively.

DETAILED DESCRIPTION

Figure 9:
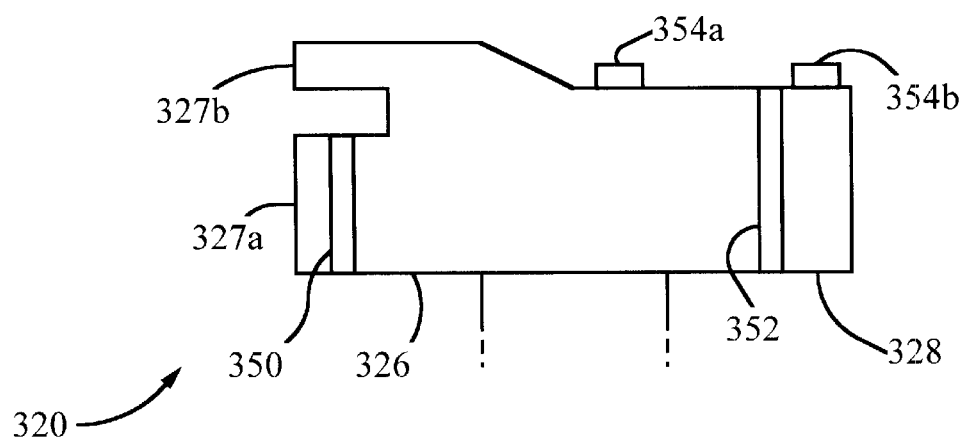
FIG. 9 shows a top schematic views of part of a respiratory control device according to an alternative embodiment of the present invention.

In the following description, the term "intermediate resistive load" is understood to refer to a resistive load between the maximum and minimum resistive loads applied during the operation of a system of the present invention. Intermediate resistive loads are understood to be deliberately applied for finite, controlled periods of time, and are not merely incidental to the rapid opening or closing of a valve. The term "butterfly valve" is understood to refer to a valve having an occluding structure capable of pivoting about a central axis perpendicular to the local direction of gas flow. The statement that a patient's respiration is controlled dynamically is understood to mean that a resistive load is imposed in the patient's respiratory path in real time in response to an electric signal characterizing the magnitude of the resistive load. The terms "electronics" and "control unit" are understood to encompass any combinations of hardware and software—special-purpose hardware and programmed general-purpose hardware. The statement that a valve has a certain response time is understood to mean that the valve is capable of moving between its extreme positions (fully open/fully shut) within that response time. Actions taken according to some original data are understood to encompass actions taken according to the original data in unaltered form, as well as data derived from the original data.

The following description illustrates embodiments of the invention by way of example and not necessarily by way of limitation.

FIG. 1-A is a schematic diagram illustrating a presently preferred dynamic respiratory control system 20 of the present invention. System 20 comprises a respiratory control device 22 and a control unit 24 electrically connected to device 22. Device 22 comprises a breathing conduit 32, monitoring components 34, and an active respiratory function valve 36, all in fluidic communication with the respiratory system of patient 30.

Breathing conduit 32 provides a path for the flow of a respiratory gas from a gas source to the respiratory system of patient 30, and from patient 30 to a respiratory gas sink. The respiratory gas source and sink are preferably the atmosphere, but may include a ventilator or other devices. The respiratory gas is preferably air, but may be pure oxygen and may include other gases.

FIGS. 2-A and 2-B show schematic top and side views of device 22, respectively, showing breathing conduit 32, a monitoring device 34, and valve 36. A conventional mouthpiece 38 is attached to the proximal end of breathing conduit 32. During the operation of device 22, mouthpiece 38 is held in the patient's mouth while the patient's nose is clamped shut. Valve 36 is secured to breathing conduit 32 opposite mouthpiece 38, such that breathing conduit 32 provides a fluidic connection between the patient and valve 36. Valve 36 is preferably attached to breathing conduit 32 through an air-tight snap-on connection.

A monitoring device 34 is mounted within conduit 32, between mouthpiece 38 and valve 36. Positioning device 34 between mouthpiece 38 and valve 36 increases the accuracy of device 34. Monitoring device 34 is electrically connected to control unit 24 through a conventional electrical connection (not shown). Monitoring device 34 preferably comprises a conventional mass flow sensor such as a hot-wire anemometer, for dynamically measuring flow rates of respiratory gas through conduit 32.

Device 22 further comprises a pressure sensing device such as a pneumotachograph (pneumotach) or differential pressure transducer device, for measuring pressures within breathing conduit 32. A conventional mesh screen 42 and a pressure measurement tube 40 are connected to conduit 32 adjacent to mouthpiece 38. A mouthpiece pressure sensor (not shown) is connected to conduit 32 through tube 40. The pressure sensor measures the pressure within conduit 32 near mouthpiece 38. The mouthpiece pressure is indicative of the direction of flow within conduit 32. Outside of valve 36, device 22 is conventional. Suitable breathing conduits, mass flow sensors, pressure sensors, and associated components are available for example from SensorMedics, Yorba Linda, Calif.

Valve 36 is capable of dynamically controlling the flow of respiratory gas through conduit 32, to and from patient 30. In response to received control signals, valve 36 is capable of introducing dynamically variable resistive loads into conduit 32, thus modulating the flow rate within conduit 32 in real time. Valve 36 is capable of completely opening/closing within 100 ms (milliseconds), preferably in less than 50 ms, ideally in 10–30 ms.

Preferably, valve 36 has a relatively good resolution, i.e. ability to finely modulate the flow rates to and from patient 30. Finely modulating the flow rates allows tightly controlling the volume within the patient's lungs and the motion of the patient's lungs and/or other internal organs. Control over organ motion is particularly desirable in treatment applications such as highly localized radiation and laser therapy. Valve 36 is preferably capable of constraining the patient volume within 100 ml, ideally 10–50 ml or less. A fast and sensitive valve allows dynamically controlling the respiration and lung volume of patient 30 in response to variable patient breathing efforts. Valve 36 is also relatively robust, such that its time and volume sensitivities do not substantially degrade over a large number of operation (breathing) cycles. Valve 36 is preferably on the order of 2–3 cm in diameter for adult patients, and about 1–2 cm in diameter for infants or small children.

Valve 36 is preferably a butterfly valve. Other fast valves such as iris (with or without seals), solenoid, and scissors valves are also suitable for use with the present invention. Iris valves allow reducing the transfer of gas associated with valve closures and openings. Potentially relevant valve parameters include minimum resistive load imposed on flows, variability of resistance, response time, maximum shutoff pressure, valve size, torque required to move, full range motion distance, difficulty in designing a suitable seal, torque required to hold the seal, and complexity of development and/or manufacturing. Butterfly valves offer a small size, simple design, low minimum resistance to flow, and good flow variability and speed.

FIGS. 3-A and 3-B show isometric and top plan views, respectively, of a preferred butterfly valve 36. Valve 36 comprises a main valve housing 44 defining a flow channel 46. A shaft (pivot) 48 is mounted within valve housing 44. Shaft 48 is perpendicular to the local, direction of respiratory gas flow within flow channel 46. An occluding structure 50 is rotatably mounted on shaft 48, for controllably occluding channel 46. Structure 50 pivots around shaft 48 between fully open and fully closed positions. The position of structure 50 determines the resistive load imposed by valve 36 on the flow of respiratory gas through channel 46. The fully open position corresponds to a minimal resistive load, while the fully closed position corresponds to a maximal resistive load.

As shown in FIG. 3-B, a digital encoder 52 is mechanically coupled to shaft 48 and housing 44. The body of encoder 52 is secured to housing 44, while its code wheel is coupled to shaft 48. An adapter 54 couples valve shaft 48 to the shaft of a motor 58. Motor 58 is a conventional DC motor with pulse-width-modulated (PWM) control. The housing of motor 58 is secured to a mounting plate 60. Mounting plate 60 is in turn secured to valve housing 44 by screws (not shown). The screws extend through holes 62 and 64 in mounting plate 60 and valve housing 44, respectively, as shown in FIG. 3-A. Encoder 52 and motor 58 are electrically connected to control unit 24 (not shown). Control unit 24 controls DC motor 58, and receives from encoder 52 digital data indicative of the position of shaft 48. The position of shaft 48 is in turn indicative of the position of valve 36.

FIGS. 4-A and 4-B show front and side sectional views, respectively, of valve 36 in its fully open position. As illustrated in FIG. 4-B, structure 50 comprises two flaps 50a–b symmetrically mounted on opposite sides of shaft 48. Flaps 50a–b have corresponding major surfaces 66a–b for occluding the flow of respiratory gas through corresponding apertures 68a–b. The effective sizes of apertures 68a–b can be varied by rotating shaft 48.

FIGS. 5-A and 5-B show front and side sectional views, respectively, of valve 36 in its fully closed position. When valve 36 is closed, flaps 50a–b establish two separate seals along corresponding closed sealing perimeters 72a–b. Sealing perimeters 72a–b are situated at the interface between major surfaces 66a–b and protruding edges 74a–b. Edges 74a–b protrude from housing 44 into channel 46, to allow the establishment of seals along major surfaces 66a–b. Protrusions 74a–b are lined with an elastomeric or foam material along sealing perimeters 72a–b, for facilitating the establishment of a seal along perimeters 72a–b. Establishing seals along major surfaces 66a–b removes the need for a soft sealing material along the edges of occluding structure 50. The major-surface seals allow reducing the minimal resistive load imposed by valve 36.

Referring back to FIG. 1, control unit 24 comprises dynamic respiratory control electronics for receiving data from device 22 and for dynamically controlling the operation device 22. Control unit 24 comprises measurement electronics 38 electrically connected to flow monitoring components 34, valve control electronics 40 electrically connected to measurement electronics 38 and valve 36, and a personal computer 44 electrically connected to control electronics 40. Personal computer 44 serves as a processing/control device, for determining resistive loads to be imposed by valve 36 according to monitoring data received from measurement electronics 38. Personal computer 44 also serves as an input and output device, for displaying and transmitting monitoring and control data, and for receiving processing instructions. Generally, the different components of control unit 24 may be spatially separated or integrated in a single housing. Generally, control unit 24 may be implemented using dedicated special-purpose hardware or may be integrated in a general-purpose computer, as will be apparent to the skilled artisan.

Control unit 24 receives from device 22 monitoring data including motor shaft position, flow rate, and/or pressure information. Control unit 24 then sends motor drive signals to motor 58 for controlling valve 36 to apply desired inspiratory and/or expiratory resistive loads according to the received monitoring data and stored information and instructions.

In the preferred embodiment, control unit 24 periodically determines the patient's current lung volume. Preferably, measurement electronics 38 integrate flow rate data over time to generate the patient's current volume. The integration step employs pressure data indicative of flow directions. Control unit 24 is then capable of applying a predetermined resistive load for each patient lung volume, according to a stored table of inspiratory and/or expiratory resistive load values to be imposed at specific lung volumes during inspiration and/or expiration. Control unit 24 can then also dynamically adjust the imposed resistive load so as to establish a desired time-dependence for the patient lung volume. Control unit 24 may determine the applied resistive load according to other parameters such as time, flow rates, or mouthpiece pressures.

FIG. 1-B shows a control unit 24' according to an alternative embodiment of the present invention. Control unit 24' comprises triggering electronics 39 electrically connected to measurement electronics 38 and to an external imaging and/or treatment device 41. Imaging/treatment device 41 can be a computer tomography (CT), magnetic resonance imaging (MRI), laser therapy, or radiotherapy device. Output signals produced by triggering electronics 39 are used to trigger the imaging/therapeutic functions of the external device 41 at predetermined patient lung volumes. Measurement electronics 38, control electronics 40, and PC 44 may also transmit measurement or valve control data to an external imaging or therapy device.

In a particular application, system 20 constrains the patient's lung volume between two predetermined values. Desired resistive loads may be applied at the same time. FIGS. 6-A through 6-C are flowcharts illustrating a preferred method of dynamically controlling valve 36 for such an application.

FIG. 6-A shows a subroutine 100 for determining whether the patient is inhaling or exhaling. Subroutine 100 preferably runs in the background of the main program controlling the operation of valve 36, and executes with a frequency of at least 20 Hz (every 50 ms). If the flow rate measured by monitoring device 34 (shown in FIG. 2-A) is higher than a predetermined positive threshold, the patient is inhaling. If the flow rate measured by monitoring device 34 is lower than a predetermined negative threshold, the patient is exhaling. If the flow rate is not measurable, the mouth pressure measured through tube 40 (see FIG. 2-A) is used to determine whether the patient is trying to inhale or exhale. If the mouth pressure is higher than a predetermined positive threshold, the patient is trying to exhale. If the mouth pressure is lower than predetermined negative threshold, the patient is trying to inhale. If the mouth pressure measurement is inconclusive, subroutine 100 uses the last known inhalation state.

The results of subroutine 100 are used in a subroutine 102 illustrated in FIG. 6-B. Subroutine 102 ensures that the patient's lung volume is maintained between two predetermined values. Subroutine 102 runs periodically in the background. If the patient is inhaling or trying to inhale and the lung volume has exceeded the maximum allowable limit, control unit 24 fully closes valve 36. Similarly, control unit 24 fully closes valve 36 if the patient's lung volume is below the minimum allowable limit and the patient is exhaling or trying to exhale. Otherwise, subroutine 102 allows the main program of control unit 24 to maintain control of the position of valve 36.

FIG. 6-C shows a main program 104 for controlling the position of valve 36 in a time-dependent fashion. The index n refers to the position of valve 36, and thus the resistive load imposed by valve 36. At each valve position (n), program 104 checks whether a timer has expired and whether the patient's breathing direction has changed. If the patient's breathing direction changes, program 104 checks whether the patient is inhaling or exhaling, and then enters the appropriate inhalation or exhalation loop. The valve position (n) is incremented at predetermined timer intervals.

The dependence of (n) with time determines the resistive load pattern imposed by valve 36.

Generally, the step of incrementing n can be dependent on any measured or derived parameters characterizing time, flow rates, patient lung volumes, or pressures. If it is desired to control valve 36 in a volume-dependent fashion, the step of incrementing n is made dependent on the current patient lung volume. The timer conditions of program 104 can be removed. The discomfort felt by the patient during sudden openings and closures of valve 36 can be reduced by gradually increasing the applied resistive load before a maximal (valve-closure) resistive load is applied to close valve 36. The index n is incremented to apply a plurality of increasing resistive loads approaching the maximal resistive load.

FIG. 7-A schematically illustrates the time variation of the volume in the patient's lungs for a method in which a patient's respiration is constrained around discrete volume levels $V_{1-3}$ for predetermined time periods. For the method shown in FIG. 7-A, the volume in the patient's lungs is used to control the timing of the closures and openings of valve 36. For example, valve 36 is closed whenever the volume in the patient's lungs approaches/reaches a volume level $V_1+\Delta V_1$. Similarly, valve 36 is closed whenever the volume in the patient's lungs approaches/reaches volume $V_1$. Valve 36 is otherwise at least partially open. The patient's respiratory function can be evaluated for each breathing regime. The evaluation can include measurements of flow rates, mouth pressures, and CT or MRI imaging. The evaluation data is then recorded and analyzed. The method illustrated in FIG. 7-A limits the motion of the patient's organs during imaging or therapy, without requiring the patient to hold his or her breath for extended periods of time.

FIG. 7-B illustrates schematically three potential dependencies of resistive load on lung volume. Each of the resistive load patterns may be applied during either or both inspiration and expiration. The first is a stairstep function, with higher resistive loads introduced at higher lung volumes. The second is a quasi-continuous linear function, with higher loads introduced at higher lung volumes. The third is a quasi-continuous curved (e.g. sinusoidal) function, with a maximal load introduced at an intermediate lung volume. For each of the illustrated resistive load patterns, the patient's respiratory function can be evaluated and measurement data can be sent to an external imaging or therapy device.

FIG. 7-C shows a potential variation of an inspiratory or expiratory resistive load with time over multiple breaths. The resistive load pattern includes stairsteps, step functions, and continuous functions. Additional forcing functions affecting breathing volumes or rates are also possible. Such varying resistive loads are useful for ventilator management or respiratory muscle training, for example for weaning a patient off a ventilator. Such varying loads may also be used for respiratory function evaluation or for triggering external devices.

FIGS. 8-A and 8-B show top and side views of a respiratory control device 222 according to an alternative embodiment of the present invention. Device 220 comprises a T-shaped conduit 224 defining the side walls of an inspiratory limb 226, an expiratory limb 228, and a mouthpiece limb 230. Arrows 244a–b illustrate the directions of air flow through device 220. Mouthpiece limb 230 includes a mouthpiece 240 defining a mouthpiece aperture 242. A cylindrical central supporting piston or hub 246 runs longitudinally through the center of limbs 226, 228. Hub 246 is connected to the walls of limbs 226, 228 through radial spokes 248. Hub 246 and spokes 248 serve to provide mechanical stability to conduit 224 within limbs 226, 228.

An active inlet (inspiratory control) valve 250 is mounted within inspiratory limb 226, for controllably occluding the passage of air through limb 226. An active outlet (expiratory control) valve 252 is mounted within expiratory limb 228, for controllably occluding the passage of air through limb 228. Valves 250, 252 are capable of independently introducing dynamically variable resistive loads into limbs 226, 228, respectively. Mouthpiece limb 230 includes a mass flow sensor 254, a mouthpiece pressure connection tube 256, and a mesh screen 257. Valves 250, 252 and sensor 254 are electrically connected to control unit 24.

Valves 250, 252 are iris valves. FIG. 8-C shows a front view of valve 250 in its fully closed position, while FIG. 8-D, shows valve 250 in its fully open position. Valve 252 is similar to valve 250, but can be operated independently of valve 250. Valve 250 comprises a plurality of overlapping blades (leaflets) 251. As shown in FIG. 8-C, blades 251 are capable of extending into the opening of limb 226, occluding the passage of air therethrough. When valve 250 is fully closed, blades 251 abut hub 246. Blades 251 are also capable of retracting from the opening of limb 226, allowing relatively unrestricted air flow through limb 226. Extending blades 251 partially into the opening of limb 226 allows introducing desired forcing functions (resistive loads) into limb 226. The forcing functions can be accurately modulated to control the inlet/outlet flow rates at specific lung volumes, as explained above.

FIG. 9 illustrates another alternative embodiment of the present invention. An inspiratory limb 326 and an expiratory limb 328 form part of a device 320. Inspiratory limb 326 comprises plural parallel air/gas channels 327a–b. An active inlet valve 350 is positioned within channel 327a but not within channel 327b. Channel 327b may be connected to a different gas source than channel 327a, such as an air, oxygen, or other gas source, or to a gas source at higher-than-atmospheric pressure. An active outlet valve 352 is positioned within limb 328.

Device 320 comprises plural pressure and/or flow sensors 354a–b all connected to the control unit of the device. Sensors 354a–b can be situated at various locations within limbs 326, 328. Sensor 354a is situated at the interface between limbs 326 and 128. Sensor 354b is positioned within expiratory limb 328, externally relative to valve 352. Data from all sensors 354a–b may be used to control the resistive loads imposed by valves 350, 352.

It will be clear to one skilled in the art that the above embodiments may be altered in many ways without departing from the scope of the invention. Measuring the patient's lung volume need not require integrating a flow rate over time. Single or multiple active valves of various types can be used. Multiple valves may be independently controlled. Passive one-way valves may be used in conjunction with one or more active valves. A Pito tube, Flesch differential pressure or other known devices may be used for pressure measurements. Accordingly, the scope of the invention should be determined by the following claims and their legal equivalents.

What is claimed is:

1. A respiratory training apparatus for performing respiratory muscle training on a patient, comprising:
   a respiratory function valve for dynamically controlling a respiratory gas flow for a patient;
   a flow rate monitoring device positioned in a flow path of said respiratory gas, in fluidic communication with said valve, for measuring a flow rate of said respiratory gas; and a control unit electrically connected to said flow rate monitoring device, and said valve, and programmed to perform the steps of:

receiving flow rate data from said flow rate monitoring device, dynamically determining patient lung volume data from said flow rate data at each of a plurality of patient lung volumes in a breathing cycle, selecting a plurality of predetermined respiratory training resistive load patterns to be applied to said patient, each respiratory training resistive load pattern defining a plurality of respiratory training resistive loads each to be applied at a patient lung volume value said plurality of resistive loads including a maximal resistive load, a minimal resistive load, and at least one intermediate resistive load higher than said minimal resistive load and lower than said maximal resistive load, and for dynamically controlling said valve to apply said plurality of respiratory training resistive load patterns to said respiratory gas flow according to said lung volume data.

2. The apparatus of claim 1 wherein said control unit comprises electronics for dynamically controlling said valve to apply an intermediate inspiratory resistive load and an intermediate expiratory resistive load to said flow.

3. The apparatus of claim 1 wherein said control unit comprises electronics for dynamically controlling said valve to maintain a lung volume of said patient between a first predetermined value and a second predetermined value.

4. The apparatus of claim 1 wherein said control unit comprises electronics for dynamically controlling said valve to apply a plurality of intermediate resistive loads to said flow.

5. The apparatus of claim 1 wherein said control unit comprises electronics for controlling said resistive load to establish a predetermined time-dependence of a lung volume of said patient.

6. The apparatus of claim 1 wherein said monitoring device comprises a mass flow sensor.

7. The apparatus of claim 1 further comprising a treatment device electrically connected and responsive to said control unit, wherein said control unit comprises electronics for triggering said treatment device at a predetermined lung volume of said patient.

8. The apparatus of claim 7, wherein the treatment device is selected from a laser therapy and a radiotherapy device.

9. The apparatus of claim 1 further comprising a patient imaging device electrically connected and responsive to said control unit, wherein said control unit comprises electronics for triggering said patient imaging device at a predetermined lung volume of said patient.

10. The apparatus of claim 9, wherein the patient imaging device is selected from a CT and an MRI device.

11. The apparatus of claim 1 wherein said valve is a butterfly valve.

12. The apparatus of claim 11 wherein said butterfly valve comprises an occluding structure having at least two occluding flaps mounted on opposite sides of a rotatable shaft.

13. The apparatus of claim 11 wherein said butterfly valve comprises an occluding structure having a rigid scaling perimeter along a major surface of said occluding structure.

14. The apparatus of claim 1 wherein said valve is selected from an iris valve, a solenoid valve, and a scissors valve.

15. The apparatus of claim 1 wherein said valve has a response time of less than 100 ms.

16. The apparatus of claim 1, wherein the control unit comprises electronics for dynamically controlling the valve to maintain the lung volume sequentially between a plurality of upper and lower value pairs.

17. The apparatus of claim 16 further comprising a treatment device electrically connected to the control unit, wherein the control unit comprises electronics for triggering the treatment device at a plurality of lung volumes of the patient.

18. The apparatus of claim 16 further comprising a patient imaging device electrically connected to the control unit, wherein the control unit comprises electronics for triggering the patient imaging device at a plurality of lung volumes of the patient.

19. The apparatus of claim 1 further comprising a pressure sensor positioned in a path of said flow and electrically connected to said control unit, for monitoring a pressure of said flow.

20. A respiratory training method for performing respiratory training on a patient, comprising:

measuring a flow rate of a respiratory gas for the patient;

dynamically determining a patient lung volume from the flow rate at each of a plurality of patient lung volumes in a breathing cycle;

selecting a plurality of predetermined respiratory training resistive load patterns to be applied to the patient, each respiratory training resistive load pattern defining a plurality of respiratory training resistive loads each to be applied at a patient lung volume value, said plurality of resistive loads including a maximal resistive load, a minimal resistive load, and at least one intermediate resistive load higher than the minimal resistive load and lower than the maximal resistive load; and applying the plurality of respiratory training resistive load patterns to the respiratory gas according to the lung volume.

21. The method of claim 20 comprising dynamically controlling said valve to apply an intermediate inspiratory resistive load and an intermediate expiratory resistive load to said flow.

22. The method of claim 20 comprising dynamically controlling said valve to maintain a lung volume of said patient between a first predetermined value and a second predetermined value.

23. The method of claim 20 comprising dynamically controlling said valve to apply a plurality of intermediate resistive loads to said flow.

24. The method of claim 20 comprising controlling said resistive load to establish a predetermined time-dependence of a lung volume of said patient.

25. The method of claim 20 wherein said flow rate data comprises a mass flow rate.

26. The method of claim 25 further comprising monitoring a pressure of said flow.

27. The method of claim 20 further comprising triggering a treatment device at a predetermined lung volume of said patient.

28. The method of claim 20 further comprising triggering a patient imaging device at a predetermined lung volume of said patient.

29. The method of claim 20 wherein said valve is a butterfly valve.

30. The method of claim 29 wherein said butterfly valve comprises an occluding structure having at least two occluding flaps mounted on opposite sides of a rotatable shaft.

31. The method of claim 29 further comprising establishing a seal along a major surface of an occluding structure of said valve, said seal occluding said flow.

32. The method of claim 20 wherein said valve is selected from an iris valve, a solenoid valve, and a scissors valve.

33. The method of claim 20 wherein said valve has a response time of less than 100 ms.

34. The method of claim 20, further comprising dynamically controlling the valve to maintain the volume sequentially between a plurality of upper and lower value pairs.

35. The method of claim 34 further comprising a treatment device electrically connected to the control unit, wherein the control unit comprises electronics for triggering the treatment device at a plurality of lung volumes of the patient.

36. The method of claim 34 comprising a patient-imaging device electrically connected to the control unit, wherein the control unit comprises electronics for triggering the patient imaging device at a plurality of lung volumes of the patient.

37. A respiratory training apparatus for performing respiratory muscle training on a patient, comprising:

a respiratory function valve for dynamically controlling a respiratory gas flow for a patient;

flow rate monitoring means positioned in a flow path of the respiratory gas, in fluidic communication with the valve, for measuring a flow rate of the respiratory gas; and control means electrically connected to the flow rate monitoring means and the valve, and programmed to perform the steps of:

receiving flow rate data from the flow rate monitoring means, dynamically determining patient lung volume data from the flow rate data at each of a plurality of patient lung volumes in a breathing cycle, selecting a plurality of predetermined respiratory training resistive load patterns to be applied to the patient, each respiratory training resistive load pattern including a maximal resistive load, a minimal resistive load, and at least one intermediate resistive load higher than the minimal resistive load and lower than the maximal resistive load, and for dynamically controlling the valve to apply the plurality of respiratory training resistive load patterns to the respiratory gas flow according to the lung volume data.

* * * * *